United States Patent
Abe et al.

(10) Patent No.: US 11,952,584 B2
(45) Date of Patent: Apr. 9, 2024

(54) FUNCTIONAL PEPTIDES HAVING ANTIMICROBIAL ACTIVITY AGAINST PHYTOPATHOGENIC MICROORGANISMS

(71) Applicants: TOYOTA JIDOSHA KABUSHIKI KAISHA, Toyota (JP); KYUSHU INSTITUTE OF TECHNOLOGY, Kitakyushu (JP); NATIONAL UNIVERSITY CORPORATION TOKAI NATIONAL HIGHER EDUCATION AND RESEARCH SYSTEM, Nagoya (JP); CHUBU UNIVERSITY EDUCATIONAL FOUNDATION, Kasugai (JP)

(72) Inventors: Madoka Abe, Nagoya (JP); Satoshi Kondo, Miyoshi (JP); Takehiko Shimada, Nagoya (JP); Kosuke Hanada, Fukuoka (JP); Keiko Mochida, Nagoya (JP); Takashi Tsuge, Kasugai (JP)

(73) Assignees: TOYOTA JIDOSHA KABUSHIKI KAISHA, Toyota (JP); KYUSHU INSTITUTE OF TECHNOLOGY, Kitakyushu (JP); NATIONAL UNIVERSITY CORPORATION TOKAI NATIONAL HIGHER EDUCATION RESEARCH SYSTEM, Nagoya (JP); CHUBU UNIVERSITY EDUCATIONAL FOUNDATION, Kasugai (JP)

(*) Notice: Subject to any disclaimer, the term of this patent is extended or adjusted under 35 U.S.C. 154(b) by 94 days.

(21) Appl. No.: 17/436,822

(22) PCT Filed: Mar. 6, 2020

(86) PCT No.: PCT/JP2020/009813
§ 371 (c)(1),
(2) Date: Sep. 7, 2021

(87) PCT Pub. No.: WO2020/184469
PCT Pub. Date: Sep. 17, 2020

(65) Prior Publication Data
US 2022/0177906 A1 Jun. 9, 2022

(30) Foreign Application Priority Data
Mar. 8, 2019 (JP) .................................. 2019-042524

(51) Int. Cl.
*C12N 15/82* (2006.01)
*C07K 14/705* (2006.01)

(52) U.S. Cl.
CPC ........ *C12N 15/8281* (2013.01); *C07K 14/705* (2013.01); *C12N 15/8282* (2013.01)

(58) Field of Classification Search
None
See application file for complete search history.

(56) References Cited

U.S. PATENT DOCUMENTS

| | | | |
|---|---|---|---|
| 4,940,840 | A | 7/1990 | Suslow et al. |
| 7,041,808 | B2 | 5/2006 | Tomie et al. |
| 7,465,783 | B2 | 12/2008 | Gallois et al. |
| 7,713,531 | B2 | 5/2010 | Takakura |
| 8,865,967 | B2 | 10/2014 | English et al. |
| 2012/0054911 | A1 | 3/2012 | English et al. |

FOREIGN PATENT DOCUMENTS

| | | |
|---|---|---|
| JP | 2004-329215 A | 11/2004 |
| JP | 2006-512052 A | 4/2006 |
| JP | 4257119 A | 4/2009 |
| JP | 4257119 B2 | 4/2009 |
| JP | 5988200 B2 | 9/2016 |
| WO | 03/033532 A1 | 4/2003 |

OTHER PUBLICATIONS

Amanatides et al. Accession No. Q9V813, deposited 2002.*
Hayashi et al. Accession: F91185, deposited 2004.*
Brown et al. Accession No. F3Z341, deposited 2011.*
Salzberg et al. Accession No. Q4EDA5, deposited 2005.*
Sagehashi et al., "Partial peptides from rice defensin OsAFP1 exhibited antifungal activity against the rice blast pathogen *Pyricularia oryzae*", J. Pestic. Sci., 2017, vol. 42, No. 4, pp. 172-175 (4 pages total).

* cited by examiner

*Primary Examiner* — Medina A Ibrahim
(74) *Attorney, Agent, or Firm* — Sughrue Mion, PLLC

(57) ABSTRACT

Antimicrobial activity exhibited against a wide variety of plant pathogens. A functional peptide consisting of the amino acid sequence: YYGFPAFSERTRKFWRIWKGKTS (SEQ ID NO: 1) or an amino acid sequence having an identity of 85% or more with respect to the amino acid sequence, or consisting of a partial peptide thereof.

10 Claims, 3 Drawing Sheets

Specification includes a Sequence Listing.

SEQUENCE LISTING

<160> NUMBER OF SEQ ID NOS: 40

<210> SEQ ID NO 1
<211> LENGTH: 23
<212> TYPE: PRT
<213> ORGANISM: Solanum lycopersicum

<400> SEQUENCE: 1

Tyr Tyr Gly Phe Pro Ala Phe Ser Glu Arg Thr Arg Lys Phe Trp Arg
1               5                   10                  15

Ile Trp Lys Gly Lys Thr Ser
            20

<210> SEQ ID NO 2
<211> LENGTH: 8
<212> TYPE: PRT
<213> ORGANISM: Solanum lycopersicum

<400> SEQUENCE: 2

Glu Arg Thr Arg Lys Phe Trp Arg
1               5

<210> SEQ ID NO 3
<211> LENGTH: 8
<212> TYPE: PRT
<213> ORGANISM: Solanum lycopersicum

<400> SEQUENCE: 3

Arg Thr Arg Lys Phe Trp Arg Ile
1               5

<210> SEQ ID NO 4
<211> LENGTH: 8
<212> TYPE: PRT
<213> ORGANISM: Solanum lycopersicum

<400> SEQUENCE: 4

Thr Arg Lys Phe Trp Arg Ile Trp
1               5

<210> SEQ ID NO 5
<211> LENGTH: 8
<212> TYPE: PRT
<213> ORGANISM: Solanum lycopersicum

<400> SEQUENCE: 5

Arg Lys Phe Trp Arg Ile Trp Lys
1               5

<210> SEQ ID NO 6
<211> LENGTH: 8
<212> TYPE: PRT
<213> ORGANISM: Solanum lycopersicum

<400> SEQUENCE: 6

Lys Phe Trp Arg Ile Trp Lys Gly
1               5

<210> SEQ ID NO 7
<211> LENGTH: 8
<212> TYPE: PRT
<213> ORGANISM: Solanum lycopersicum

<400> SEQUENCE: 7

Phe Trp Arg Ile Trp Lys Gly Lys
1               5

<210> SEQ ID NO 8
<211> LENGTH: 8
<212> TYPE: PRT
<213> ORGANISM: Solanum lycopersicum

<400> SEQUENCE: 8

Trp Arg Ile Trp Lys Gly Lys Thr
1               5

<210> SEQ ID NO 9
<211> LENGTH: 5
<212> TYPE: PRT
<213> ORGANISM: Solanum lycopersicum

<400> SEQUENCE: 9

Arg Lys Phe Trp Arg
1               5

<210> SEQ ID NO 10
<211> LENGTH: 5
<212> TYPE: PRT
<213> ORGANISM: Solanum lycopersicum -continued

<400> SEQUENCE: 10

Lys Phe Trp Arg Ile
1               5

<210> SEQ ID NO 11
<211> LENGTH: 5
<212> TYPE: PRT
<213> ORGANISM: Solanum lycopersicum

<400> SEQUENCE: 11

Trp Arg Ile Trp Lys
1               5

<210> SEQ ID NO 12
<211> LENGTH: 65
<212> TYPE: PRT
<213> ORGANISM: Solanum lycopersicum

<400> SEQUENCE: 12

Met Asp Phe Ile Met Leu Ala Ala Ala Ile Val Lys Glu Ser Phe Ile
1               5                   10                  15

Phe Leu Leu Ile Gly Leu Leu Ala Ala Ile Leu Leu Ser Leu Glu Ile
            20                  25                  30

Phe Glu Arg Lys Phe Ser Arg Ser Val Trp Tyr Tyr Gly Phe Pro Ala
        35                  40                  45

Phe Ser Glu Arg Thr Arg Lys Phe Trp Arg Ile Trp Lys Gly Lys Thr
    50                  55                  60

Ser
65

<210> SEQ ID NO 13
<211> LENGTH: 22
<212> TYPE: PRT
<213> ORGANISM: Solanum lycopersicum

<400> SEQUENCE: 13

Ile Leu Leu Ser Leu Glu Ile Phe Glu Arg Lys Phe Ser Arg Ser Val
1               5                   10                  15

Trp Tyr Tyr Gly Phe Pro
            20

<210> SEQ ID NO 14
<211> LENGTH: 40
<212> TYPE: PRT
<213> ORGANISM: Solanum lycopersicum

<400> SEQUENCE: 14

Ile Leu Leu Ser Leu Glu Ile Phe Glu Arg Lys Phe Ser Arg Ser Val
1               5                   10                  15

Trp Tyr Tyr Gly Phe Pro Ala Phe Ser Glu Arg Thr Arg Lys Phe Trp
            20                  25                  30

Arg Ile Trp Lys Gly Lys Thr Ser
        35                  40

<210> SEQ ID NO 15
<211> LENGTH: 8
<212> TYPE: PRT
<213> ORGANISM: Solanum lycopersicum

```
<400> SEQUENCE: 15

Tyr Tyr Gly Phe Pro Ala Phe Ser
1               5

<210> SEQ ID NO 16
<211> LENGTH: 8
<212> TYPE: PRT
<213> ORGANISM: Solanum lycopersicum

<400> SEQUENCE: 16

Tyr Gly Phe Pro Ala Phe Ser Glu
1               5

<210> SEQ ID NO 17
<211> LENGTH: 8
<212> TYPE: PRT
<213> ORGANISM: Solanum lycopersicum

<400> SEQUENCE: 17

Gly Phe Pro Ala Phe Ser Glu Arg
1               5

<210> SEQ ID NO 18
<211> LENGTH: 8
<212> TYPE: PRT
<213> ORGANISM: Solanum lycopersicum

<400> SEQUENCE: 18

Phe Pro Ala Phe Ser Glu Arg Thr
1               5

<210> SEQ ID NO 19
<211> LENGTH: 8
<212> TYPE: PRT
<213> ORGANISM: Solanum lycopersicum

<400> SEQUENCE: 19

Pro Ala Phe Ser Glu Arg Thr Arg
1               5

<210> SEQ ID NO 20
<211> LENGTH: 8
<212> TYPE: PRT
<213> ORGANISM: Solanum lycopersicum

<400> SEQUENCE: 20

Ala Phe Ser Glu Arg Thr Arg Lys
1               5

<210> SEQ ID NO 21
<211> LENGTH: 8
<212> TYPE: PRT
<213> ORGANISM: Solanum lycopersicum

<400> SEQUENCE: 21

Phe Ser Glu Arg Thr Arg Lys Phe
1               5

<210> SEQ ID NO 22
<211> LENGTH: 8
<212> TYPE: PRT
<213> ORGANISM: Solanum lycopersicum
```

```
<400> SEQUENCE: 22

Ser Glu Arg Thr Arg Lys Phe Trp
1               5

<210> SEQ ID NO 23
<211> LENGTH: 8
<212> TYPE: PRT
<213> ORGANISM: Solanum lycopersicum

<400> SEQUENCE: 23

Arg Ile Trp Lys Gly Lys Thr Ser
1               5

<210> SEQ ID NO 24
<211> LENGTH: 5
<212> TYPE: PRT
<213> ORGANISM: Solanum lycopersicum

<400> SEQUENCE: 24

Tyr Tyr Gly Phe Pro
1               5

<210> SEQ ID NO 25
<211> LENGTH: 5
<212> TYPE: PRT
<213> ORGANISM: Solanum lycopersicum

<400> SEQUENCE: 25

Tyr Gly Phe Pro Ala
1               5

<210> SEQ ID NO 26
<211> LENGTH: 5
<212> TYPE: PRT
<213> ORGANISM: Solanum lycopersicum

<400> SEQUENCE: 26

Gly Phe Pro Ala Phe
1               5

<210> SEQ ID NO 27
<211> LENGTH: 5
<212> TYPE: PRT
<213> ORGANISM: Solanum lycopersicum

<400> SEQUENCE: 27

Phe Pro Ala Phe Ser
1               5

<210> SEQ ID NO 28
<211> LENGTH: 5
<212> TYPE: PRT
<213> ORGANISM: Solanum lycopersicum

<400> SEQUENCE: 28

Pro Ala Phe Ser Glu
1               5

<210> SEQ ID NO 29
<211> LENGTH: 5
<212> TYPE: PRT
<213> ORGANISM: Solanum lycopersicum
```

```
<400> SEQUENCE: 29

Ala Phe Ser Glu Arg
1               5

<210> SEQ ID NO 30
<211> LENGTH: 5
<212> TYPE: PRT
<213> ORGANISM: Solanum lycopersicum

<400> SEQUENCE: 30

Phe Ser Glu Arg Thr
1               5

<210> SEQ ID NO 31
<211> LENGTH: 5
<212> TYPE: PRT
<213> ORGANISM: Solanum lycopersicum

<400> SEQUENCE: 31

Ser Glu Arg Thr Arg
1               5

<210> SEQ ID NO 32
<211> LENGTH: 5
<212> TYPE: PRT
<213> ORGANISM: Solanum lycopersicum

<400> SEQUENCE: 32

Glu Arg Thr Arg Lys
1               5

<210> SEQ ID NO 33
<211> LENGTH: 5
<212> TYPE: PRT
<213> ORGANISM: Solanum lycopersicum

<400> SEQUENCE: 33

Arg Thr Arg Lys Phe
1               5

<210> SEQ ID NO 34
<211> LENGTH: 5
<212> TYPE: PRT
<213> ORGANISM: Solanum lycopersicum

<400> SEQUENCE: 34

Thr Arg Lys Phe Trp
1               5

<210> SEQ ID NO 35
<211> LENGTH: 5
<212> TYPE: PRT
<213> ORGANISM: Solanum lycopersicum

<400> SEQUENCE: 35

Phe Trp Arg Ile Trp
1               5

<210> SEQ ID NO 36
<211> LENGTH: 5
<212> TYPE: PRT
<213> ORGANISM: Solanum lycopersicum
```

```
<400> SEQUENCE: 36

Arg Ile Trp Lys Gly
1               5

<210> SEQ ID NO 37
<211> LENGTH: 5
<212> TYPE: PRT
<213> ORGANISM: Solanum lycopersicum

<400> SEQUENCE: 37

Ile Trp Lys Gly Lys
1               5

<210> SEQ ID NO 38
<211> LENGTH: 5
<212> TYPE: PRT
<213> ORGANISM: Solanum lycopersicum

<400> SEQUENCE: 38

Trp Lys Gly Lys Thr
1               5

<210> SEQ ID NO 39
<211> LENGTH: 5
<212> TYPE: PRT
<213> ORGANISM: Solanum lycopersicum

<400> SEQUENCE: 39

Lys Gly Lys Thr Ser
1               5

<210> SEQ ID NO 40
<211> LENGTH: 22
<212> TYPE: PRT
<213> ORGANISM: Solanum lycopersicum

<400> SEQUENCE: 40

Tyr Tyr Gly Phe Pro Ala Phe Ser Glu Arg Thr Arg Lys Phe Trp Arg
1               5                   10                  15

Ile Trp Lys Gly Lys Thr
            20
```

FUNCTIONAL PEPTIDES HAVING ANTIMICROBIAL ACTIVITY AGAINST PHYTOPATHOGENIC MICROORGANISMS

CROSS REFERENCE TO RELATED APPLICATIONS

This application is a National Stage of International Application No. PCT/JP2020/009813, filed Mar. 6, 2020, claiming priority based on Japanese Patent Application No. 2019-042524, filed Mar. 8, 2019.

TECHNICAL FIELD

The present invention relates to a functional peptide exhibiting antimicrobial activity against plant pathogens such as plant pathogenic filamentous fungi, and also to an agricultural chemical comprising the functional peptide, and a method for controlling plant pathogens using the functional peptide.

BACKGROUND ART

A reduction in crop yield due to plant disease contributes to the food problem. In order to increase the crop yield, it is necessary to prevent plants from plant pathogens by using pesticides. In recent years, what is called, environmental conservation-type agriculture, in which the used amounts of agricultural chemicals or chemical fertilizers comprising chemical substances as main ingredients have been reduced, has been promoted. Thus, it has been desired to develop a substance suitable for such environmental conservation-type agriculture, which is used instead of chemical substances.

Such a substance is, for example, a peptidic substance consisting of 100 or less amino acids. Among others, defensin has been known as a peptide having antimicrobial activity that is derived from plants. It has been reported that defensin is a basic protein containing a large amount of cysteine and is present in many plant species. However, defensin is problematic in that it needs to maintain its higher-order structure in order to express antimicrobial activity, and also in that, since it is a relatively long peptide consisting of 40 or more amino acids, it is difficult to synthesize defensin and thus is expensive. Non Patent Literature 1 discloses the results obtained by synthesizing a partial peptide of rice-derived defensin and then studying the antimicrobial activity thereof. However, the partial peptide of defensin disclosed in Non Patent Literature 1 has exhibited only effects on rice blast disease, damping-off disease, rice Bakanae disease.

Moreover, Patent Literature 1 discloses that a defensin gene derived from cabbage and Japanese mustard spinach belonging to Brassicaceae is introduced into a plant, so that combined disease resistance can be imparted to the plant. Patent Literature 2 discloses isolation of a peptide having antimicrobial activity derived from *Arabidopsis*. Patent Literature 3 discloses a peptide having antimicrobial activity against *Magnaporthe oryzae*, which is extracted from *Pleurotus cornucopiae* var. *citrinopileatus* that is one type of edible mushroom. Patent Literature 4 discloses 10 to 16 partial peptides having antimicrobial activity, which have been designed from rice-derived defensin-like proteins having antimicrobial activity. Patent Literature 5 discloses isolation of a peptide having antimicrobial activity derived from *Arabidopsis*. Patent Literature 6 discloses an antimicrobial peptide consisting of 40 to 66 amino acids, which has been prepared from the body fluid of rhinoceros beetle larva. Patent Literature 7 discloses a method of performing DNA shuffling on a defensin gene to obtain an antimicrobial peptide against plant pathogens.

CITATION LIST

Patent Literature

PTL 1: JP 2004-329215 A
PTL 2: JP 2006-512052 A
PTL 3: Japanese Patent No. 4257119
PTL 4: Japanese Patent No. 5988200
PTL 5: Japanese Patent No. 4445855
PTL 6: WO 2003/033532
PTL 7: U.S. Pat. No. 8,865,967

Non Patent Literature

NPL 1: J. Pestic. Sci. 42(4), 172-175, 2017

SUMMARY OF INVENTION

Technical Problem

However, a short functional peptide that has antimicrobial activity against a wide variety of plant pathogens and is easily synthesized has not yet been known. Hence, it is an object of the present invention to consider the aforementioned circumstances and to provide a functional peptide having antimicrobial activity against a wide variety of plant pathogens, a nucleic acid encoding the functional peptide, an agricultural chemical comprising the functional peptide, and a method for controlling plant pathogens using the functional peptide.

Solution to Problem

In order to achieve the aforementioned object, the present inventor has conducted intensive studies. As a result, the present inventor has identified a peptide having antimicrobial activity against a wide variety of plant pathogens, from among peptides that have been specifically expressed in the xylem sap of tomatoes inoculated with wilt disease pathogens, thereby completing the present invention.

The present invention encompasses the following.

(1) A functional peptide consisting of the amino acid sequence: YYGFPAFSERTRKFWRIWKGKTS (SEQ ID NO: 1) or an amino acid sequence having an identity of 85% or more with respect to the amino acid sequence, or consisting of 5 or more consecutive amino acids in the amino acid sequence as set forth in SEQ ID NO: 1.

(2) The functional peptide according to the above (1), wherein the 5 or more consecutive amino acids are within a range of 9 to 22 amino acid residues counted from the N-terminus of the amino acid sequence as set forth in SEQ ID NO: 1.

(3) The functional peptide according to the above (1), wherein it consists of one amino acid sequence selected from the group consisting of the following (a) to (j):

```
                                          (SEQ ID NO: 2)
    (a) amino acid sequence: ERTRKFWR, (SEQ ID NO: 3)
    (b) amino acid sequence: RTRKFWRI,
```

```
                                                  (SEQ ID NO: 4)
(c) amino acid sequence: TRKFWRIW, (SEQ ID NO: 5)
(d) amino acid sequence: RKFWRIWK, (SEQ ID NO: 6)
(e) amino acid sequence: KFWRIWKG, (SEQ ID NO: 7)
(f) amino acid sequence: FWRIWKGK, (SEQ ID NO: 8)
(g) amino acid sequence: WRIWKGKT, (SEQ ID NO: 9)
(h) amino acid sequence: RKFWR, (SEQ ID NO: 10)
(i) amino acid sequence: KFWRI,
and (SEQ ID NO: 11)
(j) amino acid sequence: WRIWK.
```

(4) A nucleic acid encoding the functional peptide according to any one of the above (1) to (3).

(5) A recombinant vector having the nucleic acid according to the above (4).

(6) A transformant having the recombinant vector according to the above (5).

(7) The transformant according to the above (6), wherein it is a plant cell or a plant body transformed with the recombinant vector.

(8) A composition exhibiting sterilizing action or antimicrobial action against plant pathogens comprising the functional peptide according to any one of the above (1) to (3).

(9) An agricultural chemical comprising the functional peptide according to any one of the above (1) to (3).

(10) The agricultural chemical according to the above (9), which is for sterilizing or antimicrobial use against plant pathogens.

(11) The agricultural chemical according to the above (10), wherein the plant pathogens are one or more plant pathogenic filamentous fungi selected from the group consisting of *Botrytis cinerea, Colletotrichum destructivum, Colletotrichum orbiculare, Fusarium oxysporum,* and *Pyricularia oryzae.*

(12) The agricultural chemical according to the above (10), wherein the plant pathogen is *Xanthomonas oryzae* pv. *oryzae* or *Pseudomonas syringae* pv. *tomato.*

Advantageous Effects of Invention

The functional peptide according to the present invention has excellent antimicrobial activity against a wide variety of plant pathogens, and also, can be easily synthesized. As such, the functional peptide according to the present invention can be used, for example, as a composition or an agricultural chemical having sterilizing action or antimicrobial action against plant pathogens.

In addition, by using a nucleic acid encoding the functional peptide according to the present invention, the functional peptide can be expressed in a host. A plant cell or a plant body expresses the above-described functional peptide, so that resistance to a wide variety of plant pathogens can be improved.

DESCRIPTION OF EMBODIMENTS

<Functional Peptide>

Figure 1:
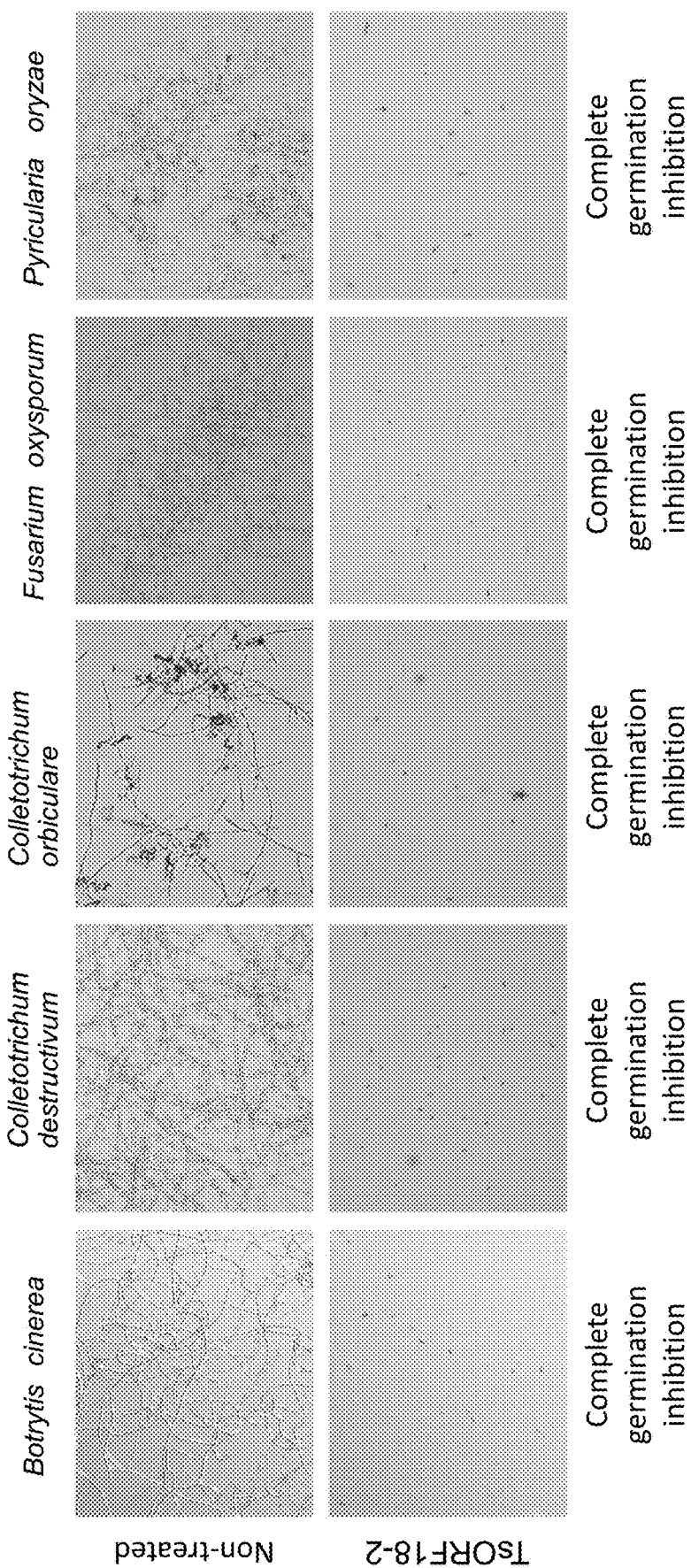
FIG. 1 shows photographs showing the results obtained by evaluating the antimicrobial activity of TsORF18-2 against five types of plant pathogenic filamentous fungi.

The functional peptide according to the present invention consists of the amino acid sequence as set forth in SEQ ID NO: 1, YYGFPAFSERTRKFWRIWKGKTS, or an amino acid sequence having an identity of 85% or more with respect to the aforementioned amino acid sequence. Herein, peptides, which are contained in xylem saps collected from tomatoes infected with wilt disease and xylem saps collected from non-infected tomatoes, have been comprehensively analyzed, and as a result, the amino acid sequence as set forth in SEQ ID NO: 1 has been identified as a peptide having antimicrobial activity against a wide variety of plant pathogens. That is to say, the functional peptide according to the present invention, at least, has a function such as antimicrobial activity against plant pathogens. Accordingly, the functional peptide according to the present invention can be used as an agricultural chemical or an agricultural chemical composition, based on its antimicrobial activity against plant pathogens.

The amino acid sequence having an identity of 85% or more with respect to the amino acid sequence as set forth in SEQ ID NO: 1 specifically means an amino acid sequence comprising a deletion, substitution or addition of 1 to 3 amino acids with respect to the amino acid sequence as set forth in SEQ ID NO: 1. The functional peptide according to the present invention has an identity of preferably 90% or more, and more preferably 95% or more, to the amino acid sequence as set forth in SEQ ID NO: 1. It is highly likely that an amino acid sequence having this range of identity to the amino acid sequence as set forth in SEQ ID NO: 1 exhibits antimicrobial activity against plant pathogens, as with the peptide consisting of the amino acids shown in SEQ ID NO: 1.

In particular, the amino acid sequence comprising a deletion, substitution or addition of 1 to 3 amino acids with respect to the amino acid sequence as set forth in SEQ ID NO: 1 is not particularly limited, but the position in which 1 to 3 amino acids are deleted, substituted or added is preferably a position close to the N-terminus. More specifically, the position in which 1 to 3 amino acids are deleted, substituted or added is a position in a range from 1 to 8, and preferably from 1 to 5, counted from the N-terminus. The position in which 1 to 3 amino acids are deleted, substituted or added is set to be within this range, so that antimicrobial activity against plant pathogens can be maintained at high.

It is to be noted that an amino acid sequence different from the amino acid sequence as set forth in SEQ ID NO: 1 can be produced by introducing a desired mutation into a nucleic acid encoding the amino acid sequence as set forth in SEQ ID NO: 1, for example, using a mutation introduction kit utilizing site-specific mutagenesis (e.g., Mutant-K (manufactured by Takara Bio, Inc.) or Mutant-G (manufactured by Takara Bio, Inc.)), or using LA PCR in vitro Mutagenesis Series Kit of Takara Bio, Inc.

By the way, the functional peptide according to the present invention is not limited to a functional peptide consisting of the amino acid sequence as set forth in SEQ ID NO: 1 (a length of 23 amino acid residues), but it may also consist of consecutive 5 or more amino acids from the amino acid sequence as set forth in SEQ ID NO: 1. Hereafter, the peptide consisting of consecutive 5 or more amino acids from the amino acid sequence as set forth in SEQ ID NO: 1 is also referred to as a partial peptide in some cases. An example of this partial peptide may be, but is not limited to, a peptide consisting of consecutive 5 to 15 amino acids, preferably consecutive 5 to 10 amino acids, more preferably consecutive 5 to 8 amino acids, and further preferably consecutive 8 amino acids, selected from the amino acid sequence as set forth in SEQ ID NO: 1.

In particular, such a partial peptide is selected from a range from 9 to 22 amino acid residues, preferably a range from 10 to 22 amino acid residues, and more preferably a range from 11 to 20 amino acid residues, counted from the N-terminus of the amino acid sequence as set forth in SEQ ID NO: 1. When the partial peptide has an amino acid sequence in the aforementioned range, it can exhibit more excellent antimicrobial activity.

More specifically, the partial peptide is preferably one selected from the group consisting of the following (a) to (j). The following partial peptides can exhibit particularly excellent antimicrobial activity against plant pathogens:

```
                                              (SEQ ID NO: 2)
(a) amino acid sequence: ERTRKFWR, (SEQ ID NO: 3)
(b) amino acid sequence: RTRKFWRI, (SEQ ID NO: 4)
(c) amino acid sequence: TRKFWRIW, (SEQ ID NO: 5)
(d) amino acid sequence: RKFWRIWK, (SEQ ID NO: 6)
(e) amino acid sequence: KFWRIWKG, (SEQ ID NO: 7)
(f) amino acid sequence: FWRIWKGK, (SEQ ID NO: 8)
(g) amino acid sequence: WRIWKGKT, (SEQ ID NO: 9)
(h) amino acid sequence: RKFWR, (SEQ ID NO: 10)
(i) amino acid sequence: KFWRI,
and (SEQ ID NO: 11)
(j) amino acid sequence: WRIWK.
```

The functional peptide according to the present invention (including the aforementioned partial peptides) can be easily produced according to conventionally known methods. Examples of the method of synthesizing a peptide may include a solid phase synthesis method and a liquid phase synthesis method. With regard to the solid phase synthesis method, a Fmoc method (fluorenylmethyloxycarbonyl method), a tBoc method (t-butyloxycarbonyl method), etc. is applied, so that a functional peptide having a desired amino acid sequence can be synthesized.

Moreover, the functional peptide according to the present invention can also be produced by producing a nucleic acid encoding the amino acid sequence, and then applying a genetic engineering method using the produced nucleic acid. That is, for example, a nucleic acid encoding the aforementioned functional peptide is chemically synthesized, the nucleic acid is then incorporated into an expression vector, and the thus obtained expression vector is then introduced into suitable host cells, so as to obtain a transformant. This transformant is cultured and is then allowed to generate a functional peptide, and the generated functional peptide may be then recovered from the transformant and/or the medium.

The expression vector is not particularly limited, as long as it has a nucleic acid encoding a functional peptide and can express the functional peptide in any given host cells. Examples of the expression vector may include a plasmid vector and a viral vector. Besides, the host cells are not particularly limited, and bacteria such as *Escherichia coli* or *Bacillus subtilis*, and fungi such as yeast or filamentous fungi can be utilized. Moreover, as such host cells, animal cells such as insect cells or mammalian cells may be used. For example, when *Escherichia coli* are used as host cells, an expression vector comprising, at least, a promoter region, a start codon, a nucleic acid encoding the functional peptide according to the present invention, a stop codon, a terminator region and a replication origin can be used.

The aforementioned transformant is cultured, and thereafter, the functional peptide according to the present invention can be recovered from the transformant and can be then purified. The method of isolating and purifying a functional peptide is not particularly limited. Examples of the method of isolating and purifying a functional peptide may include, but are not limited to: methods of utilizing solubility, such as salting-out and a solvent precipitation method; methods of utilizing a difference in molecular weights, such as dialysis, ultrafiltration, gel filtration, and sodium dodecyl sulfate-polyacrylamide gel electrophoresis; methods of utilizing electric charges, such as ion exchange chromatography and hydroxylapatite chromatography; methods of utilizing specific affinity, such as affinity chromatography; methods of utilizing a difference in hydrophobicity, such as reverse phase high performance liquid chromatography; and methods of utilizing a difference in isoelectric points, such as isoelectric point electrophoresis.

Furthermore, the functional peptide according to the present invention can also be produced, for example, as a histidine-tagged or Flag-tagged functional peptide, by a transformant. In this case, by using a substance having affinity for such a tag, the functional peptide can be more easily isolated and purified.

Further, the functional peptide according to the present invention can be synthesized by utilizing, what is called, a cell-free protein synthesis system. In such a cell-free protein synthesis system, an extract, for example, from *Escherichia coli*, rabbit reticulocytes, or wheat germs can be utilized.

<Antimicrobial Activity of Functional Peptide>

The functional peptide according to the present invention has antimicrobial activity against a wide variety of plant pathogens. Herein, the antimicrobial activity includes both the activity of preventing infection with plant pathogens, and sterilizing activity against plant pathogens. Examples of plant pathogens, against which the functional peptide according to the present invention exhibits antimicrobial activity, may include a wide range of plant pathogenic filamentous fungi. More specifically, examples of the plant pathogens may include plant pathogenic filamentous fungi belonging to the genus *Botrytis*, plant pathogenic filamentous fungi belonging to the genus *Colletotrichum*, plant pathogenic filamentous fungi belonging to the genus *Fusarium*, and plant pathogenic filamentous fungi belonging to the genus *Pyricularia*.

Examples of the plant pathogenic filamentous fungi belonging to the genus *Botrytis* may include *Botrytis aclada*, *Botrytis byssoidea*, *Botrytis cinerea*, *Botrytis convoluta*,

*Botrytis diospyri*, *Botrytis elliptica*, *Botrytis fabae*, *Botrytis galanthina*, *Botrytis gladiolorum*, *Botrytis paeoniae*, *Botrytis polyblastis*, *Botrytis* sp., *Botrytis squamosa*, and *Botrytis tulipae*.

Examples of the plant pathogenic filamentous fungi belonging to the genus *Colletotrichum* may include *Colletotrichum actinidiicola*, *Colletotrichum acutatum*, *Colletotrichum aenigma*, *Colletotrichum ampelopsidis*, *Colletotrichum belamcandium*, *Colletotrichum boninense sensu lato*, *Colletotrichum capsici*, *Colletotrichum carthami*, *Colletotrichum caudatum*, *Colletotrichum chrysanthemi*, *Colletotrichum circinans*, *Colletotrichum coccodes*, *Colletotrichum coffeanum*, *Colletotrichum corchori*, *Colletotrichum crassipes*, *Colletotrichum cypripedii*, *Colletotrichum daphnicola*, *Colletotrichum dematium*, *Colletotrichum destructivum*, *Colletotrichum durionis*, *Colletotrichum echinochloae*, *Colletotrichum elasticae*, *Colletotrichum fatsiae*, *Colletotrichum fioriniae*, *Colletotrichum fuscum*, *Colletotrichum gloeosporioides*, *Colletotrichum godetiae*, *Colletotrichum graminicola*, *Colletotrichum hibisci*, *Colletotrichum higginsianum*, *Colletotrichum horii*, *Colletotrichum hydrangeae*, *Colletotrichum kahawae*, *Colletotrichum karstii*, *Colletotrichum koyasuensis*, *Colletotrichum lappae*, *Colletotrichum liliacearum*, *Colletotrichum lilii*, *Colletotrichum lindemuthianum*, *Colletotrichum malvarum*, *Colletotrichum medicaginis-denticulatae*, *Colletotrichum metake*, *Colletotrichum moricola*, *Colletotrichum morinum*, *Colletotrichum musae*, *Colletotrichum nigrum*, *Colletotrichum nymphaeae*, *Colletotrichum orbiculare*, *Colletotrichum panacicola*, *Colletotrichum paniculatae*, *Colletotrichum pehkinense*, *Colletotrichum phaseolorum*, *Colletotrichum sansevieriae*, *Colletotrichum sasicola*, *Colletotrichum siamense*, *Colletotrichum sophorae-japonicae*, *Colletotrichum spaethianum*, *Colletotrichum spinaciae*, *Colletotrichum sublineolum*, *Colletotrichum tabacum*, *Colletotrichum theobromicola*, *Colletotrichum trichellum*, *Colletotrichum trifolii*, *Colletotrichum tropicale*, *Colletotrichum truncatum*, *Colletotrichum villosum*, and *Colletotrichum yoshinoi*.

Examples of the plant pathogenic filamentous fungi belonging to the genus *Fusarium* may include *Fusarium acuminatum*, *Fusarium ananatum*, *Fusarium anguioides*, *Fusarium arthrosporioides*, *Fusarium asiaticum*, *Fusarium avenaceum*, *Fusarium brasiliense*, *Fusarium commune*, *Fusarium conglutinans* var. *betae*, *Fusarium cuneirostrum*, *Fusarium decemcellulare*, *Fusarium dimerum* var. *dimerum*, *Fusarium foetens*, *Fusarium fujikuroi*, *Fusarium graminearum*, *Fusarium guttiforme*, *Fusarium lactis*, *Fusarium lagenariae*, *Fusarium lateritium*, *Fusarium merismoides*, *Fusarium oxysporum*, *Fusarium pallidoroseum*, *Fusarium pallidum*, *Fusarium phaseoli*, *Fusarium phyllophilum*, *Fusarium poae*, *Fusarium proliferatum*, *Fusarium redolens*, *Fusarium ricini*, *Fusarium roseum*, *Fusarium solani*, *Fusarium striatum*, *Fusarium subglutinans*, and *Fusarium verticillioides*.

Examples of the plant pathogenic filamentous fungi belonging to the genus *Pyricularia* may include *Pyricularia grisea*, *Pyricularia higginsii*, *Pyricularia oryzae*, *Pyricularia panici*, and *Pyricularia zingiberis*.

Other than these, examples of the plant pathogens may include plant pathogens belonging to the genus *Alternaria*, plant pathogens belonging to the genus Cladosporium, plant pathogens belonging to the genus *Claviceps*, plant pathogens belonging to the genus *Sclerotinia*, plant pathogens belonging to the genus *Septoria*, plant pathogens belonging to the genus *Pseudoperonospora*, and plant pathogens belonging to the genus *Puccinia*.

In particular, examples of plant pathogenic filamentous fungi, against which the functional peptide according to the present invention exhibits high antimicrobial activity, may include *Botrytis cinerea*, *Colletotrichum destructivum*, *Colletotrichum orbiculare*, *Fusarium oxysporum*, and *Pyricularia oryzae* (that is a synonym for Magnaporthe *oryzae*).

Moreover, the functional peptide according to the present invention has antimicrobial activity, not only against plant pathogenic filamentous fungi, but also against plant pathogenic bacteria such as *Xanthomonas oryzae* pv. *oryzae* and *Pseudomonas syringae* pv. *tomato*.

Examples of the plant pathogenic bacteria belonging to the genus *Xanthomonas* may include *Xanthomonas campestris* pv. *malloti*, *Xanthomonas axonopodis* pv. *phaseoli*, *Xanthomonas alfalfae* pv. *alfalfae*, *Xanthomonas arboricola* pv. *pruni*, *Xanthomonas translucens* pv. *poae*, *Xanthomonas campestris* pv. *fici*, *Xanthomonas oryzae* pv. *oryzae*, *Xanthomonas oryzae* pv. *oryzicola*, *Xanthomonas axonopodis* pv. *phaseoli*, *Xanthomonas translucens* pv. *translucens*, *Xanthomonas arboricola*, *Xanthomonas campestris* pv. *raphani*, *Xanthomonas campestris* pv. *campestris*, *Xanthomonas cucurbitae*, *Xanthomonas citri* subsp. *citri*, *Xanthomonas hortorum* pv. *hederae*, *Xanthomonas axonopodis* pv. *manihotis*, *Xanthomonas arboricola* pv. *juglandis*, *Xanthomonas campestris* pv. *nigromaculans*, *Xanthomonas albilineans*, *Xanthomonas axonopodis* pv. *vasculorum*, *Xanthomonas campestris*, *Xanthomonas cucurbitae*, *Xanthomonas axonopodis* pv. *glycines*, *Xanthomonas campestris* pv. *cannabis*, *Xanthomonas translucens* pv. *phleipratensis*, *Xanthomonas theicola*, *Xanthomonas vesicatoria*, *Xanthomonas euvesicatoria*, *Xanthomonas hortorum* pv. *carotae*, *Xanthomonas axonopodis* pv. *allii*, *Xanthomonas arboricola* pv. *celebensis*, *Xanthomonas axonopodis* pv. *ricini*, *Xanthomonas hortorum* pv. *pelargonii*, *Xanthomonas translucens* pv. *cerealis*, *Xanthomonas campestris* pv. *mangiferaeindicae*, *Xanthomonas vasicola* pv. *holcicola*, *Xanthomonas axonopodis* pv. *lespedezae*, *Xanthomonas translucens* pv. *cerealis*, *Xanthomonas hortorum*, *Xanthomonas axonopodis* pv. *Vitians*, and *Xanthomonas citri* subsp. *Malvacearum*.

As mentioned above, since the functional peptide according to the present invention has antimicrobial action against a wide variety of plant pathogens, it can control plant diseases caused by plant pathogens, against which the present functional peptide exhibits antimicrobial action. Specific examples of the plant diseases, which can be controlled by the functional peptide according to the present invention, may include rice diseases such as rice blast disease, sesame blight disease, sheath blight disease, rice Baka-nae disease, and bacterial leaf blight. In addition, other examples of the plant diseases, which can be controlled by the functional peptide according to the present invention, may include, are not particularly limited to: powdery mildew, fusarium blight, rust, *Microdochium nivale*, *Typhula incarnata*, smut, bare smut, stinking smut, eye spot, leaf blight, blight, *Pyrenophora tritici-repentis*, *Rhynchosporium secalis*, *Pyrenophora teres*, *Cochliobolus sativus*, *Pyrenophora graminea*, seedling damping-off disease caused by *Rhizoctonia*, zonate leaf spot, *Puccinia polysora*, gray leaf spot disease, *Cercospora kikuchii*, anthracnose, melanose, brown spot, target spot, sclerotinia rot, anthracnose, *Alternaria solani*, scarlet rot, powdery scab, and mildew.

<Agricultural Chemical and Composition Each Comprising Functional Peptide>

Since the functional peptide according to the present invention has antimicrobial action against a wide variety of plant pathogens, it can be used as an agricultural chemical or an agricultural chemical composition. Herein, the agricultural chemical composition means a composition that can be used upon the production of an agricultural chemical. For example, the functional peptide according to the present invention can be utilized as a germicide having germicidal action against plant pathogens, in particular, against plant pathogenic filamentous fungi. More specifically, a functional peptide compound may be directly used as an agricultural chemical, but in general, the functional peptide compound may be mixed with a suitable solid carrier, liquid carrier, surfactant or other formulation auxiliary agents, so that it can be used in any given dosage form such as an emulsion, an EW preparation, a liquid agent, a suspending agent, a water-dispersible powder, a water-dispersible granule, a powder agent, a DL powder agent, a microparticle agent, a microparticle agent F, a granule, a tablet, an oil agent, an aerosol, a flowable agent, a dry flowable agent, and a microcapsule.

Examples of the solid carrier may include: animal and plant powders, such as starch, activated carbon, soy flour, wheat flour, wood flour, fish flour, and powdered milk; and inorganic matter powders, such as talc, kaolin, bentonite, calcium carbonate, zeolite, diatomaceous earth, white carbon, clay, alumina, ammonium sulfate, and urea.

Examples of the liquid carrier may include: water; alcohols such as isopropyl alcohol and ethylene glycol; ketones such as cyclohexanone and methylethylketone; ethers such as dioxane and tetrahydrofuran; aliphatic hydrocarbons such as kerosene and light oil; aromatic hydrocarbons such as xylene, trimethylbenzene, tetramethylbenzene, methylnaphthalene, and solvent naphtha; halogenated hydrocarbons such as chlorobenzene; acid amides such as dimethylacetamide; esters such as glycerin esters of fatty acids; nitriles such as acetonitrile; and sulfur-containing compounds such as dimethyl sulfoxide.

Examples of the surfactant may include alkylbenzene sulfonic acid metal salts, dinaphthyl methane disulfonic acid metal salts, alcohol sulfuric acid ester salts, alkylaryl sulfonate, lignin sulfonate, polyoxyethylene glycol ether, polyoxyethylene alkylaryl ether, and polyoxyethylene sorbitan monoalkylate.

Examples of other auxiliary agents that can be used herein may include: fixing agents or thickeners, such as carboxymethyl cellulose, gum Arabic, sodium alginate, guar gum, gum tragacanth, and polyvinyl alcohol; defoaming agents, such as metal soap; physical property improving agents, such as fatty acid, alkyl phosphate, silicone, and paraffin; and coloring agents.

In general, various types of germicidal preparations or diluted products thereof can be applied by commonly used application methods, such as spraying (e.g., spraying, misting, atomizing, dusting, granule application, submerged application, box application, etc.), soil application (e.g., mixing into soil, irrigation, etc.), surface application (e.g., application, dressing, coating, etc.), immersion, use of poison baits, and smoke application.

Furthermore, needless to say, a pesticide comprising, as an active ingredient, the functional peptide according to the present invention is sufficiently effective, even when the present functional peptide is used alone. However, as necessary, the functional peptide can be mixed with, or can be used in combination with other fertilizers, agricultural chemicals such as insecticides, acaricides or nematicides, other pesticides, antiviral agents, attractants, herbicides, and plant growth regulators, and the like.

The thus configured agricultural chemical can be applied to plants that may develop plant diseases due to the aforementioned plant pathogens. Examples of the target plants may include, but are not particularly limited to: agricultural crops, such as corn, rice, wheat, barley, rye, oats, sorghum, cotton, soybeans, peanuts, soba, sugar beet, rape, sunflower, sugar cane, tobacco, solanaceous vegetables (eggplant, tomato, pimiento, pepper, potato, etc.), cucurbitaceous vegetables (cucumber, pumpkin, zucchini, watermelon, melon, squash, etc.) cruciferous vegetables (Japanese radish, turnip, horseradish, kohlrabi, Chinese cabbage, cabbage, mustard greens, broccoli, cauliflower, etc.), asteraceae vegetables (burdock, crown daisy, artichoke, lettuce, etc.), liliaceae vegetables (leek, onion, garlic, asparagus, etc.), apiaceous vegetables (carrot, parsley, celery, red wolf, etc.), chenopodiaceae vegetables (spinach, chard, etc.), mint vegetables (Japanese basil, mint, basil, etc.), strawberry, sweet potato, yam, and taro; flowers; foliage plants; turfs; fruit trees, such as pome fruits (apple, pear, Japanese pear, quince, marmelo, etc.), stone fruits (peach, plum, nectarine, Japanese plum, cherry, apricot, prune, etc.), citrus fruits (citrus unshiu, orange, lemon, lime, grapefruit, etc.), nuts (chestnuts, walnuts, hazelnuts, almonds, pistachios, cashew nuts, macadamia nuts, etc.), berry fruits (blueberry, cranberry, blackberry, raspberry, etc.), grapes, persimmon, olive, loquat, banana, coffee, date palm, coconuts, etc.; and trees other than fruit trees, such as tea, mulberry, Jatropha (Jatropha curcas), flower trees, roadside trees (ash, birch, dogwood, eucalyptus, ginkgo, lilac, maple, oak, poplar, *Cercis chinensis*, *Liquidambar formosana*, plane tree, Japanese zelkova, *Thuja standishii*, fir tree, *Tsuga sieboldii*, *Juniperus rigida*, pine tree, spruce tree, and yew tree).

Among others, the aforementioned agricultural chemical comprising the present functional peptide as an active ingredient is preferably applied to cruciferous plants, cucurbitaceous plants, and gramineous plants.

<Transformed Plant>

As mentioned above, the functional peptide according to the present invention has antimicrobial action against a wide variety of plant pathogens. Thus, a transformed plant that expresses the present functional peptide at a high level is characterized in that it exhibits resistance to the aforementioned plant diseases. The transformed plant includes both a transformed plant cell prepared by expressibly introducing a nucleic acid encoding the aforementioned functional peptide into a predetermined plant cell, and a transformed plant body prepared by regenerating the transformed plant cell in a plant body. The transformed plant according to the present invention expresses the aforementioned functional peptide, so that the resistance of the transformed plant to the aforementioned plant pathogens is improved.

More specifically, examples of the transformed plant may include, but are not particularly limited to: agricultural crops, such as corn, rice, wheat, barley, rye, oats, sorghum, cotton, soybeans, peanuts, soba, sugar beet, rape, sunflower, sugar cane, tobacco, solanaceous vegetables (eggplant, tomato, pimiento, pepper, potato, etc.), cucurbitaceous vegetables (cucumber, pumpkin, zucchini, watermelon, melon, squash, etc.) cruciferous vegetables (Japanese radish, turnip, horseradish, kohlrabi, Chinese cabbage, cabbage, mustard greens, broccoli, cauliflower, etc.), asteraceae vegetables (burdock, crown daisy, artichoke, lettuce, etc.), liliaceae vegetables (leek, onion, garlic, asparagus, etc.), apiaceous vegetables (carrot, parsley, celery, red wolf, etc.), chenopodiaceae vegetables (spinach, chard, etc.), mint vegetables (Japanese basil, mint, basil, etc.), strawberry, sweet potato, yam, and taro; flowers; foliage plants; turfs; fruit trees, such as pome fruits (apple, pear, Japanese pear, quince, marmelo, etc.), stone fruits (peach, plum, nectarine, Japanese plum, cherry, apricot, prune, etc.), citrus fruits (citrus unshiu, orange, lemon, lime, grapefruit, etc.), nuts (chestnuts, walnuts, hazelnuts, almonds, pistachios, cashew nuts, macadamia nuts, etc.), berry fruits (blueberry, cranberry, blackberry, raspberry, etc.), grapes, persimmon, olive, loquat, banana, coffee, date palm, coconuts, etc.; and trees other than fruit trees, such as tea, mulberry, Jatropha (Jatropha curcas), flower trees, roadside trees (ash, birch, dogwood, *eucalyptus*, ginkgo, lilac, maple, oak, poplar, *Cercis chinensis*, *Liquidambar formosana*, plane tree, Japanese *zelkova*, *Thuja standishii*, fir tree, *Tsuga sieboldii*, *Juniperus rigida*, pine tree, spruce tree, and yew tree).

It is to be noted that a method for producing the transformed plant according to the present invention is not particularly limited, and as a summary, a transformed plant expressing the aforementioned functional peptide can be produced according to a method comprising incorporating a nucleic acid encoding the aforementioned functional peptide into an expression vector, and then introducing the obtained expression vector into a plant.

The expression vector is configured to comprise a promoter enabling expression in a plant and a nucleic acid encoding the aforementioned functional peptide. As vectors used to produce the present expression vector, various types of conventionally known vectors can be used. For example, a plasmid, a phage, a cosmid or the like can be used, and a suitable vector can be selected from these, as appropriate, depending on a plant cell into which the vector is to be introduced, or an introduction method. Specific examples of such a vector may include vectors such as pBR322, pBR325, pUC19, pUC119, pBluescript, pBluescript SK, and pBI. In particular, when the method of introducing a vector into a plant body is a method using *Agrobacterium*, a pBI binary vector is preferably used. Specific examples of the pBI binary vector may include pBIG, pBIN19, pBI101, and pBI121.

The promoter is not particularly limited, as long as it is a promoter enabling expressing a nucleic acid encoding the above-described functional peptide in a plant body. A known promoter can be preferably used. In particular, as a promoter, it is preferable to use a constant expression promoter constantly expressing a gene located downstream thereof in a plant body. Examples of such a promoter may include a cauliflower mosaic virus 35S promoter (CaMV35S), various types of actin gene promoters, various types of ubiquitin gene promoters, a nopaline synthase gene promoter, a tobacco PR1a gene promoters, a tomato ribulose 1,5-diphosphate carboxylase oxygenase small subunit gene promoter, and a napin gene promoter. Among these promoters, a cauliflower mosaic virus 35S promoter, an actin gene promoter, or a ubiquitin gene promoter can be more preferably used. Using each of the above-described promoters, when the promoter is introduced into a plant cell, any given gene can be strongly expressed therein.

Moreover, as such a promoter, a promoter having the function of site-specifically expressing any given gene in a plant can also be used. As such promoters, any conventionally known promoters can be used. Using such promoters, the above-described functional peptide can be site-specifically expressed.

Furthermore, as a promoter, a gene promoter inducing the expression of the gene in response to disease can be used. Examples of such a promoter may include a plant defensin 1.2 (PDF1.2) gene promoter, a pathogenesis-related 1 (PR1) gene promoter, a PR2 gene promoter, and a PR5 gene promoter. Using such a promoter, the above-described functional peptide can be expressed specifically to the time of pathogenic infection.

It is to be noted that the expression vector may comprise other DNA segments, in addition to a promoter and a nucleic acid encoding the above-described functional peptide. Such other DNA segments are not particularly limited, but examples thereof may include a terminator, a selective marker, an enhancer, and a nucleotide sequence for enhancing translation efficiency. In addition, the above-described expression vector may further have a T-DNA region. The T-DNA region can enhance the efficiency of gene introduction, when the above-described recombinant expression vector is introduced into a plant body, particularly using *Agrobacterium*.

The transcription terminator is not particularly limited, as long as it functions as a transcription termination site, and a known transcription terminator may be used. For example, specifically, a transcription termination region of a napaline synthase gene (Nos terminator), a transcription termination region of cauliflower mosaic virus 35S (CaMV35S terminator), and the like can be preferably used. Among these, a Nos terminator can be more preferably used. By disposing a transcription terminator at a suitable position in the above-described expression vector, generation of a phenomenon, by which an unnecessary long transcriptional product is synthesized, can be prevented after introduction of the vector into a plant cell.

As a selective marker for selecting a transformant, for example, a drug resistance gene can be used. Specific examples of such a drug resistance gene may include drug resistance genes that are resistant to hygromycin, bleomycin, kanamycin, gentamycin, chloramphenicol, etc. Thus, by selecting a plant body that grows in a medium containing the above-described antibiotics using such a selective marker, a transformed plant body can be easily selected.

A method of constructing the expression vector is not particularly limited, either. The above-described promoter and the above-described nucleic acid encoding the functional peptide, and also, as necessary, the above-described other DNA segments may be introduced in a predetermined order into the appropriately selected vector used to produce an expression vector. For instance, a nucleic acid encoding the above-described functional peptide may be connected with a promoter (as necessary, with a transcription terminator, etc.) to construct an expression cassette, and this expression cassette may be then introduced into a vector. In construction of such an expression cassette, for example, the cleavage sites of individual DNA segments are set to be protruding ends that are complementary to one another, and they are then reacted using a ligation enzyme, so that the order of the DNA segments can be determined. When the expression cassette comprises a terminator, the positional order may be a promoter, a nucleic acid encoding the above-described functional peptide, and a terminator from the upstream thereof. Moreover, the types of reagents used to construct the expression vector, namely, the types of restriction enzymes, ligation enzymes, etc. are not particularly limited, either, and commercially available products may be selected, as appropriate, and may be then used.

The aforementioned expression vector is introduced into a target plant according to a common transformation method. The method of introducing an expression vector into a plant cell (transformation method) is not particularly limited, and a conventionally known suitable method that depends on a plant cell can be applied. Specifically, for example, a method using *Agrobacterium* or a method of directly introducing an expression vector into a plant cell can be used. Examples of the method of directly introducing an expression vector into a plant cell that can be used herein may include a microinjection method, an electroporation method, a polyethylene glycol method, a particle cancer method, a protoplast fusion method, and a calcium phosphate method.

Moreover, if a method of directly introducing DNA into a plant cell is adopted, it is sufficient for the DNA to comprise transcription units necessary for the expression of a target gene, such as, for example, a promoter and a transcription terminator, and also, a nucleic acid encoding the above-described functional peptide. Thus, it is not essential for the DNA to function as a vector. Furthermore, it may be sufficient even if DNA comprises only a coding region of the above-described functional peptide, without having transcription units, if the DNA can be integrated into the transcription units of a host and can express the functional peptide as a target therein.

Examples of the plant cell, into which the above-described expression vector or an expression cassette that does not comprise the expression vector but comprises a nucleic acid encoding the target functional peptide is to be introduced, may include the cells, callus, and suspension cultured cells of individual tissues in plant organs such as flowers, leaves, and roots. The expression vector that is used herein may be constructed, as appropriate, depending on the type of a plant body to be produced. Otherwise, a versatile expression vector may have previously been constructed, and it may be then introduced into a plant cell.

Tumor tissues, shoots, hairy roots and the like obtained as a result of the transformation can be directly used in cell culture, tissue culture or organ culture. Alternatively, according to the conventionally known plant tissue culture method, a suitable concentration of plant hormone (auxin, cytokinin, gibberellin, abscisic acid, ethylene, brassinolide, etc.) is administered to such tumor tissues and the like, so as to regenerate a plant body.

As a regeneration method, a method comprising transferring callus-like transformed cells into a medium containing different type and different concentration of hormone, then culturing the cells therein to form an adventive embryo, and then obtaining a complete plant body, is adopted. Examples of the medium used herein may include an LS medium and an MS medium.

Moreover, the transformed plant according to the present invention also includes progeny plants obtained by introducing an expression vector comprising a nucleic acid encoding the aforementioned functional peptide into host cells to obtain transformed plant cells, then regenerating a transformed plant body from the transformed plant cells, then obtaining plant seeds from the obtained transformed plant body, and then obtaining the progeny plants from the plant seeds. In order to obtain plant seeds from a transformed plant body, for example, a transformed plant body is collected from a rooting medium and is then transplanted into a pot in which water-containing soil has been placed, and thereafter, the plant body is allowed to grow under a constant temperature and to form flowers, and finally seeds are formed. Otherwise, in order to produce a plant body from a seed, for example, when seeds formed in a transformed plant body have become mature, the seeds are isolated, are then seeded on soil containing water, and are then allowed to grow under a constant temperature and constant illumination, thereby producing plant bodies. The thus produced plant expresses the aforementioned functional peptide, and thus exhibits excellent resistance to the aforementioned plant pathogens.

Examples

Hereinafter, the present invention will be described in more detail in the following examples. However, the following examples are not intended to limit the technical scope of the present invention.

In the present example, functional peptides having antimicrobial activity against plant pathogenic filamentous fungi and partial peptides thereof were identified in the following order.

1. Collection of xylem saps of tomatoes infected/not-infected with wilt disease
2. Proteomic analysis
3. Identification of peptides in the xylem saps
4. Synthesis of functional peptides
5. Evaluation of antimicrobial activity against plant pathogenic filamentous fungi Hereafter, the above-described procedures 1. to 5. will be successively explained.

<1. Collection of Xylem Saps of Tomatoes Infected/not Infected with Wilt Disease>

A tomato variety Ponterosa was allowed to grow in soil (Kumiai Nippi Engei Baido). A tomato seedling with two first leaves developed was dugged up, and the roots thereof were then washed with tap water. The roots were immersed in a bud cell suspension of tomato wilt disease pathogens (*Fusarium oxysporum* CK3-1 strain) ($1 \times 10^6$ cells/ml) for approximately 30 seconds, and were then transplanted in a vinyl pot containing Kumiai Nippi Engei Baido. Thereafter, the roots were allowed to grow in an environment control room (25° C., light: 14 hours, dark: 10 hours). As a control group, a non-inoculated seedling was allowed to grow in the same manner as described above. The inoculated seedling and the non-inoculated seedling were cut at a site immediately below the first leaf, 7, 9, 11, and 13 days after the transplantation. The pot was laid down, and the cross-section of the stem was placed in a 2.0-ml plastic tube. The stem was left at rest at room temperature for 12 hours, and a xylem sap leaked from each cross-section was recovered. The amount of the recovered liquid was measured, and thereafter, the liquid was then filtrated through a cellulose filter (Minisart RC15, Sartrium Stedim), and was then preserved at −80° C.

The concentration of a protein in the xylem sap was measured using Bio-Rad DC Protein Assay Kit (Bio-Rad). A calibration curve was produced using bovine serum albumin (BSA).

<2. Proteomic Analysis>

In-Gel Trypsin Digestion of Xylem Sap Protein

To a xylem sap sample (12 µl, approx. 10 µg) collected from each of the seedlings inoculated with and not-inoculated with tomato wilt disease pathogens, 4 µl of 4× sample buffer (Wako Pure Chemical Industries, Ltd.) was added, and electrophoresis of approximately 2.5 cm was then performed according to SDS-PAGE. Thereafter, the gel was divided into 6 gel sections, and the sections were further minced to sections with 1 mm square. In-gel digestion was carried out with reference to the method of Rosefeld et al. (1992) (Rosenfeld, J., Capdevielle, J., Guillemot, J. C. and Ferrara, P. (1992). In-gel digestion of proteins for internal sequence analysis after one- or two-dimensional gel electrophoresis. Anal. Biochem. 203: 173-179).

First, the gel was washed with Milli-Q water (ultrapure water) and 50 mM ammonium carbonate/50% acetonitrile each once, and was then dried and solidified with acetonitrile. 50 mM tris(2-carboxyethyl)phosphine was added to the resulting gel, and the obtained mixture was then left at rest at 60° C. for 10 minutes. Thereafter, 100 mM 2-iodoacetamide was added to the resultant, and the thus obtained mixture was then left at rest at room temperature for 1 hour. Thereafter, the resulting gel was washed with Milli-Q water (ultrapure water) and 50 mM ammonium carbonate/50% acetonitrile each once, and was then dried and solidified with acetonitrile. After that, Lys-C/trypsin (0.01 mg/ml, manufactured by Promega) was added to the gel to swell it. To the swollen gel, 20 μl of 50 mM ammonium carbonate was added, and the obtained mixture was then reacted at 37° C. for 16 hours. Using 20% trifluoroacetic acid, the reaction solution was adjusted to pH=2, and was then filtrated through 0.1-μm Durapore Membrane PVDF (manufactured by Merck Millipore), followed by vacuum concentration, and the resultant was dissolved in 0.1% trifluoroacetic acid/2% acetonitrile.

Nano LC-MS/MS Analysis

For nano-LC-MS/MS analysis, a system formed by combining Q Exactive Hybrid Quadrupole-Orbitrap Mass Spectrometer (manufactured by Thermo Fisher Scientific) with Dionex U3000 gradient pump (manufactured by Thermo Fisher Scientific) was used. A trap column (L-column ODS, 300 μm I.D.×5 mm, particle diameter: 5 μm, Chemicals Evaluation and Research Institute) and an analytical column (NTCC-360, 100 μm I.D.×125 mm, particle diameter: 3 μm, Nikkyo Technos Co., Ltd.) were used. Also, a mobile phase A (0.5% acetic acid) and a mobile phase B (0.5% acetic acid-containing 80% acetonitrile) were used. The flow rate was set at 0.5 μl/min, and the gradient was carried out with an acetonitrile concentration from 5% B to 35% B for 100 minutes, from 35% B to 100% B for 1 minute, 100% B for 3 minutes, and finally 5% B for 10 minutes.

<3. Identification of Peptide in Xylem Sap>

Proteins detected by the nano LC-MS/MS analysis were analyzed using Proteome Discoverer 2.0.0.802 (manufactured by Thermo Fisher Scientific). As database, tomato sORF database (ITAG2.4_gene_models_sORF), tomato protein database (ITAG2.4_protein), tomato wilt disease pathogen protein database (fusarium_oxysporum_f._sp._lycopersici_4827_2_protein) were used. As a result, the following peptides were discovered: 4 peptides (named as TsORF 6, 11, 19, and 29), the non-inoculated tomato-specific expression of which was confirmed; 4 peptides (named as TsORF 8, 15, 18, and 30), the inoculated tomato-specific expression of which was confirmed; and 6 peptides (named as TsORF 10, 16, 17, 21, 24, and 25), which were expressed in both non-inoculated and inoculated tomatoes.

The above-described 14 types of peptides identified in the present example were not registered in the above-described tomato protein database (ITAG2.4_protein) and tomato wilt disease pathogen protein database (fusarium_oxysporum_f._sp._lycopersici_4827_2_protein), but were registered only in the tomato sORF database (ITAG2.4_gene_models_sORF). This tomato sORF database store information regarding frames (sORFs: small open reading frames) encoding peptides consisting of 10 to 100 amino acid residues, which were found by applying the method disclosed in sORF finder: a program package to identify small open reading frames with high coding potential K Hanada, K Akiyama, T Sakurai, T Toyoda, K Shinozaki, SH Shiu Bioinformatics 26 (3), 399-400 to tomatoes and then discovering the peptides in an intergenic region that reportedly did not have a common ORF.

<4. Synthesis of Functional Peptide>

In the present example, among the peptides identified in the present example, a peptide consisting of 65 amino acid residues, which was named as "TsORF18" (mdfimlaaaivkesfiflliglIaaILLSLEIFERKFSRSVWYYGFPAFSERTRKFWRIWKGK TS: SEQ ID NO: 12) was used as an analytical target. It is to be noted that, in the above-described amino acid sequence, the region indicated with small letters corresponds to a signal peptide. A region consisting of 40 amino acid residues (TsORF18-40 a.a.), which is formed by excluding the signal peptide from the aforementioned peptide, and the following two regions (TsORF18-1 and TsORF18-2) obtained by dividing TsORF18-40 a.a., were each chemically synthesized.

```
TsORF18-1:
                                        (SEQ ID NO: 13)
ILLSLEIFERKFSRSVWYYGFP

TsORF18-2:
                                        (SEQ ID NO: 40)
YYGFPAFSERTRKFWRIWKGKT

TsORF18-40 a.a:
                                        (SEQ ID NO: 14)
ILLSLEIFERKFSRSVWYYGFPAFSERTRKFWRIWKGKTS
```

Moreover, in the present example, based on the amino acid sequence of TsORF18-2, partial peptides each consisting of 8 amino acids (Table 1) and partial peptides each consisting of 5 amino acid residues (Table 2) were designed and were then chemically synthesized.

TABLE 1

| Peptide name | Amino acid sequence | SEQ ID NO: |
|---|---|---|
| TsORF18-2-8aa-1 | YYGFPAFS | SEQ ID NO: 15 |
| TsORF18-2-8aa-2 | YGFPAFSE | SEQ ID NO: 16 |
| TsORF18-2-8aa-3 | GFPAFSER | SEQ ID NO: 17 |
| TsORF18-2-8aa-4 | FPAFSERT | SEQ ID NO: 18 |
| TsORF18-2-8aa-5 | PAFSERTR | SEQ ID NO: 19 |
| TsORF18-2-8aa-6 | AFSERTRK | SEQ ID NO: 20 |
| TsORF18-2-8aa-7 | FSERTRKF | SEQ ID NO: 21 |
| TsORF18-2-8aa-8 | SERTRKFW | SEQ ID NO: 22 |
| TsORF18-2-8aa-9 | ERTRKFWR | SEQ ID NO: 2 |
| TsORF18-2-8aa-10 | RTRKFWRI | SEQ ID NO: 3 |
| TsORF18-2-8aa-11 | TRKFWRIW | SEQ ID NO: 4 |
| TsORF18-2-8aa-12 | RKFWRIWK | SEQ ID NO: 5 |

TABLE 1-continued

| Peptide name | Amino acid sequence | SEQ ID NO: |
|---|---|---|
| TsORF18-2-8aa-13 | KFWRIWKG | SEQ ID NO: 6 |
| TsORF18-2-8aa-14 | FWRIWKGK | SEQ ID NO: 7 |
| TsORF18-2-8aa-15 | WRIWKGKT | SEQ ID NO: 8 |
| TsORF18-2-8aa-16 | RIWKGKTS | SEQ ID NO: 23 |

TABLE 2

| Peptide name | Amino acid sequence | SEQ ID NO: |
|---|---|---|
| TsORF18-2-5aa-1 | YYGFP | SEQ ID NO: 24 |
| TsORF18-2-5aa-2 | YGFPA | SEQ ID NO: 25 |
| TsORF18-2-5aa-3 | GFPAF | SEQ ID NO: 26 |
| TsORF18-2-5aa-4 | FPAFS | SEQ ID NO: 27 |
| TsORF18-2-5aa-5 | PAFSE | SEQ ID NO: 28 |
| TsORF18-2-5aa-6 | AFSER | SEQ ID NO: 29 |
| TsORF18-2-5aa-7 | FSERT | SEQ ID NO: 30 |
| TsORF18-2-5aa-8 | SERTR | SEQ ID NO: 31 |
| TsORF18-2-5aa-9 | ERTRK | SEQ ID NO: 32 |
| TsORF18-2-5aa-10 | RTRKF | SEQ ID NO: 33 |
| TsORF18-2-5aa-11 | TRKFW | SEQ ID NO: 34 |
| TsORF18-2-5aa-12 | RKFWR | SEQ ID NO: 9 |
| TsORF18-2-5aa-13 | KFWRI | SEQ ID NO: 10 |
| TsORF18-2-5aa-14 | FWRIW | SEQ ID NO: 35 |
| TsORF18-2-5aa-15 | WRIWK | SEQ ID NO: 11 |
| TsORF18-2-5aa-16 | RIWKG | SEQ ID NO: 36 |
| TsORF18-2-5aa-17 | IWKGK | SEQ ID NO: 37 |
| TsORF18-2-5aa-18 | WKGKT | SEQ ID NO: 38 |
| TsORF18-2-5aa-19 | KGKTS | SEQ ID NO: 39 |

<5. Evaluation of Antimicrobial Activity Against Plant Pathogenic Filamentous Fungi>

5-1. Plate Antimicrobial Test

In the present example, antimicrobial activity against *Botrytis cinerea, Colletotrichum destructivum, Colletotrichum orbiculare, Fusarium oxysporum*, and *Pyricularia oryzae* was evaluated by observing germination of spores. In the present example, first, 100 µl of a spore suspension (approx. $10^4$ cells) of each of these filamentous fungi was dispensed in a 96-well microplate.

Subsequently, the peptides to be tested (TsORF18-1, TsORF18-2, TsORF18-40 a.a., TsORF18 (full length), and partial peptides of TsORF18-2 (Tables 1 and 2)) were each added into individual wells. It is to be noted that the concentration of the peptide was set at 1 µM, 10 µM or 100 µM. Thereafter, the peptides were cultured at 25° C. for 1 day or 2 days.

After completion the culture, each well was observed under a microscope, and the antimicrobial activity of the tested peptides was evaluated. In the present example, antimicrobial activity was defined to be levels 0 to 3 in an ascending order. As a result of the microscopic observation, a case where hyphae extended to the entire well and no antimicrobial activity was found is defined as "level 0," a case where hyphae extended to less than a half of the well and thus the peptide inhibited the growth of the hyphae is defined as "level 1," a case where ungerminated spores were present and the peptide partially inhibited the germination is defined as "level 2," and a case where all spores were ungerminated and the peptide completely inhibited the germination is defined as "level 3."

As an example, the microscopic observation results of TsORF18-2 are shown in FIG. 1. Besides, the photographs shown in the upper case of FIG. 1 indicate non-treated controls. As shown in FIG. 1, when TsORF18-2 was used, all of *Botrytis cinerea, Colletotrichum destructivum, Colletotrichum orbiculare, Fusarium oxysporum* and *Pyricularia oryzae* were completely inhibited in terms of germination.

5-2. *Botrytis cinerea* Leaf Inoculation Test

In the present example, a suspension comprising *Botrytis cinerea* and a peptide to be tested was dropped on a plant leaf, and lesions were then observed by visual inspection to evaluate the antimicrobial activity of the tested peptide.

First, the pores of *Botrytis cinerea* were suspended in a potato dextrose broth (PDB) to result in a spore concentration of $5 \times 10^5$ spores/ml, so as to prepare a PDB suspension spore solution. Subsequently, a peptide to be tested (TsORF18-2) was added to the PDB suspension spore solution, so that the final concentration of the peptide to be tested became 0 µM, 1 µM, 10 µM or 100 µM. It is to be noted that, as peptides to be tested, TsORF18 (full length) and TsORF18-40 a.a. were also used in the same manner as that of TsORF18-2. TsORF18 (full length) was dissolved in DMSO and was then used. On the other hand, TsORF18-2 and TsORF18-40 a.a were each dissolved in Milli-Q water and were then used.

Figure 2:
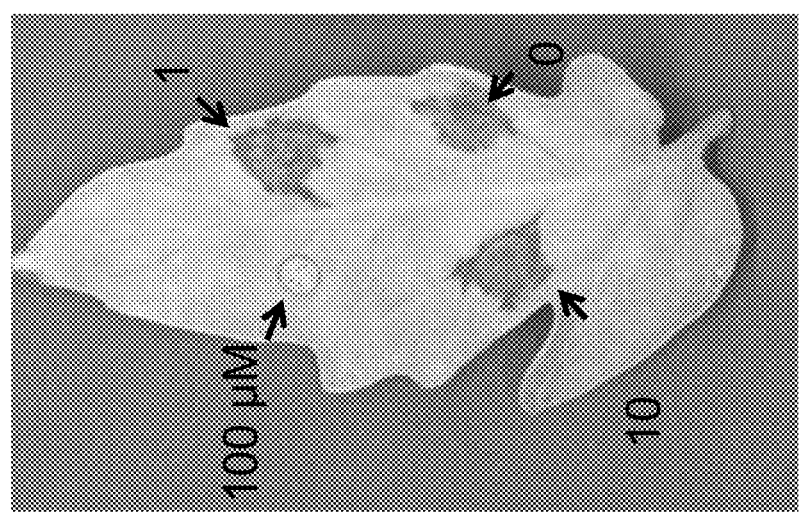
FIG. 2 is a photograph showing the results obtained by inoculating TsORF18-2, together with *Botrytis cinerea*, into the leaves of tomatoes.

Thereafter, 10 µl each of the PDB suspension spore solution containing the peptide to be tested was dropped on the front side and the back side of the leaf of tomato (variety name: "Ponte Rosa"). In this condition, incubation was carried out at 25° C. for 2 days. Thereafter, the front and back sides of the leaf were observed by visual inspection. A photograph of the front and back sides of the leaf is shown in FIG. 2. As shown in FIG. 2, even if the PDB suspension spore solution containing 100 μM TsORF18-2 was dropped on the leaf, a lesion of *Botrytis cinerea* was not observed. From these results, it became clear that 100 μM TsORF18-2 exhibited extremely excellent antimicrobial activity against *Botrytis cinerea*.

Although it is not shown in the figures, the inhibitory effects against *Botrytis cinerea* were not observed in the case of using TsORF18 (full length) and also in the case of using TsORF18-40 a.a.

5-3. *Colletotrichum destructivum* Leaf Inoculation Test

In the present example, a suspension comprising *Colletotrichum destructivum* and a peptide to be tested was dropped on a plant leaf, and lesions were then observed by visual inspection to evaluate the antimicrobial activity of the tested peptide.

First, the pores of *Colletotrichum destructivum* were suspended in water to result in a spore concentration of $5 \times 10^5$ spores/ml, so as to prepare a water suspension of spores. Subsequently, peptides to be tested (TsORF18 (full length), TsORF18-40 a.a., and TsORF18-2) were each added to the water suspension of spores, so that the final concentration of the peptides to be tested became 0 μM, 1 μM, 10 μM or 100 μM.

Figure 3:
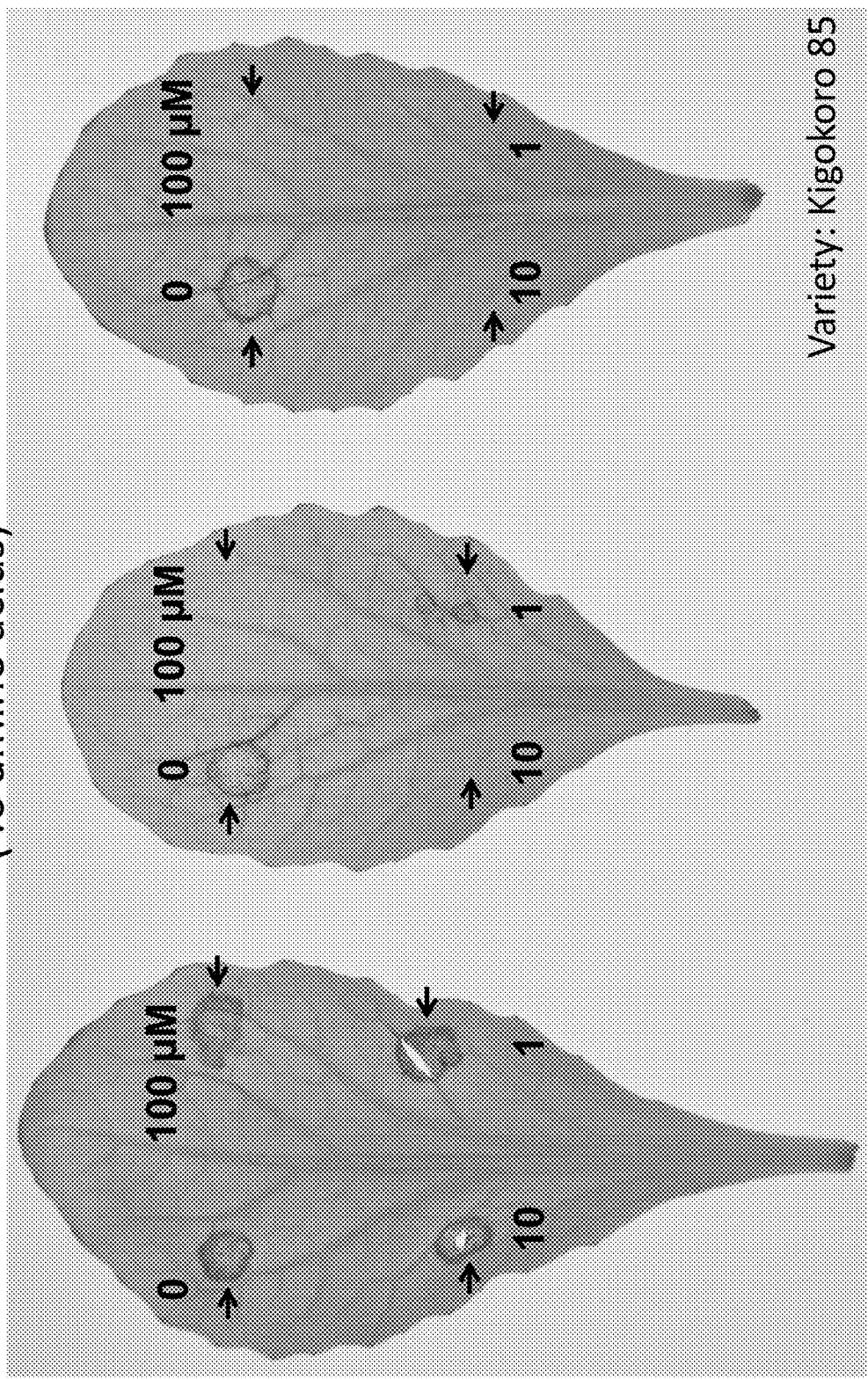
FIG. 3 is a photograph showing the results obtained by inoculating TsORF18-2, together with *Colletotrichum destructivum*, into the leaves of Chinese cabbages.

Thereafter, 10 μl each of the water suspension of spores containing the peptide to be tested was dropped on the front side and the back side of the leaf of Chinese cabbage (variety name: "Kigokoro 85"). In this condition, incubation was carried out at 25° C. for 4 days. Thereafter, the front and back sides of the leaf were observed by visual inspection. A photograph of the front sides of the leaves is shown in FIG. 3. As shown in FIG. 3, when TsORF18-2 was dropped on the leaves in any concentration of 1 μM, 10 μM or 100 μM, a lesion of *Colletotrichum destructivum* was not observed. On the other hand, in the case of using TsORF18 (full length), a lesion of *Colletotrichum destructivum* was observed in any concentration of TsORF18 (full length). However, in the case of using TsORF18-40 a.a. prepared by excluding a signal peptide from the full-length TsORF18, such a lesion of *Colletotrichum destructivum* was not observed in a concentration of 10 μM or 100 μM.

From these results, it became clear that TsORF18-2 and TsORF18-40 a.a. exhibit extremely excellent antimicrobial activity against *Colletotrichum destructivum*.

5-4. Antimicrobial Tests Against Other Plant Pathogens

In the present example, antimicrobial activity against *Ralstonia solanacearum, Erwinia carotovora* subsp. *carotovora, Xanthomonas oryzae* pv. *oryzae*, and *Pseudomonas syringae* pv. *tomato* was evaluated. In the present example, first, these microorganisms were cultured, and 100 μl of the culture solution ($OD_{600}=0.1$) was dispensed in a 96-well microplate.

Subsequently, the peptide to be tested was added to each well to result in a final concentration of 100 μM. In addition, as a negative control, water was added instead of the peptide to be tested. Thereafter, the obtained mixture was cultured at 28° C. a whole day and night, and the value of $OD_{600}$ was then measured. Using the measured $OD_{600}$ value, the proliferation percentage was calculated according to the following equation:

[Proliferation percentage (%)]=(1−$OD_{600[peptide\ added]}$)/$OD_{600[water\ added]} \times 100$ 5-5. Results The experimental results of the above-described sections 5-1, 5-2 and 5-3 are summarized in Table 3.

TABLE 3

| | | Plant pathogenic filamentous fungi | | | | | | | | | | | | | | | | | | | | |
|---|---|---|---|---|---|---|---|---|---|---|---|---|---|---|---|---|---|---|---|---|---|---|
| | | Plate antimicrobial activity test | | | | | | | | | | | | | | | Leaf inoculation test | | | | | |
| | | | | | | | | | | | | | | | | | Tomato/ Botrytis cinerea (μM) | | | Chinese cabbage/ Colletotrichum destructivum (μM) | | |
| | | Botrytis cinerea (μM) | | | Colletotrichum destructivum (μM) | | | Collectotrichum orbiculare (μM) | | | Fusarium oxysporum (μM) | | | Pyricularia oryzae (μM) | | | | | | | | |
| | | 100 | 10 | 1 | 100 | 10 | 1 | 100 | 10 | 1 | 100 | 10 | 1 | 100 | 10 | 1 | 100 | 10 | 1 | 100 | 10 | 1 |
| TsORF18-1 | Approx. | 0 | 0 | 0 | 0 | 0 | 0 | 0 | 0 | 0 | 0 | 0 | 0 | 0 | 0 | 0 | — | — | — | — | — | — |
| TsORF18-2 | 20 amino acids | 3 | 3 | 1 | 3 | 2 | 0 | 3 | 1 | 0 | 3 | 1 | 0 | 3 | 0 | 0 | ○ | x | x | ○ | ○ | ○ |
| TsORF18-40aa | 40 amino acids | 3 | 0 | 0 | 3 | 0 | 0 | — | — | — | 3 | 0 | 0 | — | — | — | x | — | — | ○ | ○ | Δ |
| TsORF18 | 65 amino acids (total chain) | 0 | 0 | 0 | 1 | 0 | 0 | — | — | — | 0 | 0 | 0 | — | — | — | x | — | — | x | x | x |
| TsORF18-2-8aa-1 | 8 amino acids | 0 | 0 | 0 | 0 | 0 | 0 | 0 | 0 | 0 | 0 | 0 | 0 | 0 | 0 | 0 | x | — | — | x | — | — |
| TsORF18-2-8aa-2 | | 0 | 0 | 0 | 0 | 0 | 0 | 0 | 0 | 0 | 0 | 0 | 0 | 0 | 0 | 0 | x | — | — | x | — | — |
| TsORF18-2-8aa-3 | | 0 | 0 | 0 | 0 | 0 | 0 | 0 | 0 | 0 | 0 | 0 | 0 | 0 | 0 | 0 | x | — | — | x | — | — |
| TsORF18-2-8aa-4 | | 0 | 0 | 0 | 0 | 0 | 0 | 0 | 0 | 0 | 0 | 0 | 0 | 0 | 0 | 0 | x | — | — | x | — | — |
| TsORF18-2-8aa-5 | | 0 | 0 | 0 | 0 | 0 | 0 | 0 | 0 | 0 | 0 | 0 | 0 | 0 | 0 | 0 | x | — | — | x | — | — |
| TsORF18-2-8aa-6 | | 0 | 0 | 0 | 0 | 0 | 0 | 0 | 0 | 0 | 0 | 0 | 0 | 0 | 0 | 0 | x | — | — | x | — | — |

TABLE 3-continued

| | | Plant pathogenic filamentous fungi | | | | | | | | | | | | | | | | | | | | |
|---|---|---|---|---|---|---|---|---|---|---|---|---|---|---|---|---|---|---|---|---|---|---|
| | | Plate antimicrobial activity test | | | | | | | | | | | | | | | Leaf inoculation test | | | | | |
| | | | | | | | | | | | | | | | | | Tomato/ | | | Chinese cabbage/ | | |
| | | *Botrytis cinerea* (μM) | | | *Colletotrichum destructivum* (μM) | | | *Collectotrichum orbiculare* (μM) | | | *Fusarium oxysporum* (μM) | | | *Pyricularia oryzae* (μM) | | | *Botrytis cinerea* (μM) | | | *Colletotrichum destructivum* (μM) | | |
| | | 100 | 10 | 1 | 100 | 10 | 1 | 100 | 10 | 1 | 100 | 10 | 1 | 100 | 10 | 1 | 100 | 10 | 1 | 100 | 10 | 1 |
| TsORF18-2-8aa-7 | | 0 | 0 | 0 | 0 | 0 | 0 | 0 | 0 | 0 | 0 | 0 | 0 | 0 | 0 | 0 | x | — | — | x | — | — |
| TsORF18-2-8aa-8 | | 0 | 0 | 0 | 0 | 0 | 0 | 0 | 0 | 0 | 0 | 0 | 0 | 0 | 0 | 0 | x | — | — | x | — | — |
| TsORF18-2-8aa-9 | | 3 | 0 | 0 | 0 | 0 | 0 | 1 | 0 | 0 | 3 | 0 | 0 | 1 | 0 | 0 | x | — | — | x | — | — |
| TsORF18-2-8aa-10 | | 3 | 0 | 0 | 3 | 0 | 0 | 3 | 0 | 0 | 3 | 1 | 0 | 1 | 0 | 0 | x | — | — | ○ | ○ | x |
| TsORF18-2-8aa-11 | | 3 | 0 | 0 | 3 | 0 | 0 | 3 | 0 | 0 | 3 | 3 | 0 | 0 | 0 | 0 | ○ | x | x | ○ | ○ | x |
| TsORF18-2-8aa-12 | | 3 | 1 | 0 | 3 | 0 | 0 | 3 | 0 | 0 | 3 | 2 | 0 | 0 | 0 | 0 | ○ | x | x | ○ | ○ | Δ |
| TsORF18-2-8aa-13 | | 3 | 0 | 0 | 3 | 0 | 0 | 3 | 0 | 0 | 3 | 2 | 0 | 0 | 0 | 0 | ○ | x | x | ○ | ○ | x |
| TsORF18-2-8aa-14 | | 3 | 0 | 0 | 3 | 0 | 0 | 3 | 0 | 0 | 3 | 0 | 0 | 0 | 0 | 0 | x | — | — | ○ | ○ | Δ |
| TsORF18-2-8aa-15 | | 3 | 0 | 0 | 3 | 0 | 0 | 3 | 0 | 0 | 3 | 0 | 0 | 0 | 0 | 0 | x | — | — | x | — | — |
| TsORF18-2-8aa-16 | | 2 | 0 | 0 | 0 | 0 | 0 | 1 | 0 | 0 | 1 | 0 | 0 | 0 | 0 | 0 | x | — | — | x | — | — |
| TsORF18-2-5aa-1 | 5 amino acids | 0 | 0 | 0 | 0 | 0 | 0 | 0 | 0 | 0 | 0 | 0 | 0 | 0 | 0 | 0 | x | — | — | x | — | — |
| TsORF18-2-5aa-2 | | 0 | 0 | 0 | 0 | 0 | 0 | 0 | 0 | 0 | 0 | 0 | 0 | 0 | 0 | 0 | x | — | — | x | — | — |
| TsORF18-2-5aa-3 | | 0 | 0 | 0 | 0 | 0 | 0 | 0 | 0 | 0 | 0 | 0 | 0 | 0 | 0 | 0 | x | — | — | x | — | — |
| TsORF18-2-5aa-4 | | 0 | 0 | 0 | 0 | 0 | 0 | 0 | 0 | 0 | 0 | 0 | 0 | 0 | 0 | 0 | x | — | — | x | — | — |
| TsORF18-2-5aa-5 | | 0 | 0 | 0 | 0 | 0 | 0 | 0 | 0 | 0 | 0 | 0 | 0 | 0 | 0 | 0 | x | — | — | x | — | — |
| TsORF18-2-5aa-6 | | 0 | 0 | 0 | 0 | 0 | 0 | 0 | 0 | 0 | 0 | 0 | 0 | 0 | 0 | 0 | x | — | — | x | — | — |
| TsORF18-2-5aa-7 | | 0 | 0 | 0 | 0 | 0 | 0 | 0 | 0 | 0 | 0 | 0 | 0 | 0 | 0 | 0 | x | — | — | x | — | — |
| TsORF18-2-5aa-8 | | 0 | 0 | 0 | 0 | 0 | 0 | 0 | 0 | 0 | 0 | 0 | 0 | 0 | 0 | 0 | x | — | — | x | — | — |
| TsORF18-2-5aa-9 | | 0 | 0 | 0 | 0 | 0 | 0 | 0 | 0 | 0 | 0 | 0 | 0 | 0 | 0 | 0 | x | — | — | x | — | — |
| TsORF18-2-5aa-10 | | 1 | 0 | 0 | 0 | 0 | 0 | 0 | 0 | 0 | 0 | 0 | 0 | 0 | 0 | 0 | x | — | — | x | — | — |
| TsORF18-2-5aa-11 | | 0 | 0 | 0 | 0 | 0 | 0 | 0 | 0 | 0 | 0 | 0 | 0 | 0 | 0 | 0 | x | — | — | x | — | — |
| TsORF18-2-5aa-12 | | 3 | 0 | 0 | 3 | 0 | 0 | 2 | 0 | 0 | 3 | 0 | 0 | 0 | 0 | 0 | x | — | — | ○ | ○ | x |
| TsORF18-2-5aa-13 | | 3 | 0 | 0 | 3 | 0 | 0 | 3 | 0 | 0 | 3 | 0 | 0 | 1 | 0 | 0 | x | — | — | ○ | ○ | x |
| TsORF18-2-5aa-14 | | 0 | 0 | 0 | 0 | 0 | 0 | 0 | 0 | 0 | 0 | 0 | 0 | 0 | 0 | 0 | x | — | — | x | — | — |
| TsORF18-2-5aa-15 | | 3 | 0 | 0 | 3 | 0 | 0 | 2 | 0 | 0 | 2 | 0 | 0 | 0 | 0 | 0 | x | — | — | x | — | — |
| TsORF18-2-5aa-16 | | 0 | 0 | 0 | 0 | 0 | 0 | 0 | 0 | 0 | 0 | 0 | 0 | 0 | 0 | 0 | x | — | — | x | — | — |
| TsORF18-2-5aa-17 | | 0 | 0 | 0 | 0 | 0 | 0 | 0 | 0 | 0 | 0 | 0 | 0 | 0 | 0 | 0 | x | — | — | x | — | — |
| TsORF18-2-5aa-18 | | 0 | 0 | 0 | 0 | 0 | 0 | 0 | 0 | 0 | 0 | 0 | 0 | 0 | 0 | 0 | x | — | — | x | — | — |
| TsORF18-2-5aa-19 | | 0 | 0 | 0 | 0 | 0 | 0 | 0 | 0 | 0 | 0 | 0 | 0 | 0 | 0 | 0 | x | — | — | x | — | — |

In addition, the experimental results of the above-described section 5-4 are shown in Table 4.

TABLE 4

|  | Ralstonia solanacearum 100 μM | | Erwinia carotovora subsp. cartovora 100 μM | | Xanthomonas oryzae pv. oryzae 100 μM | | Pseudomonas syringae pv. tomato 100 μM | |
| --- | --- | --- | --- | --- | --- | --- | --- | --- |
|  | OD$_{600}$ | Inhibitory rate | OD$_{600}$ | Inhibitory rate | OD$_{600}$ | Inhibitory rate | OD$_{600}$ | Inhibitory rate |
| TsORF18-1 | — | — | — | — | — | — | — | — |
| TsORF18-2 | 2.2 | 13.8 | 2.6 | −39.2 | 0.2 | 90.1 | 1.9 | 25.3 |
| TsORF18-40a.a. | 2.8 | −7.7 | 2.2 | −18.1 | 2.2 | −5.8 | 1.9 | 25.8 |
| TsORF18(full length) | 2.6 | −0.9 | 1.9 | −3.7 | 2.0 | 6.5 | 2.6 | −3.1 |
| Water | 2.6 | — | 1.9 | — | 2.1 | — | 2.5 | — |

As shown in Tables 3 and 4, the peptide TsORF18-2 (SEQ ID NO: 40) could inhibit germination of a wide range of plant pathogenic filamentous fungi, such as *Botrytis cinerea, Colletotrichum destructivum, Colletotrichum orbiculare, Fusarium oxysporum*, and *Pyricularia oryzae*. Moreover, the peptide TsORF18-2 (SEQ ID NO: 40) could inhibit the growth of plant pathogenic bacteria, such as *Xanthomonas oryzae* pv. *oryzae* and *Pseudomonas syringae* pv. *tomato*.

Furthermore, as shown in Table 3, the partial peptides of the peptide TsORF18-2 (SEQ ID NO: 40) could inhibit germination of a wide range of plant pathogenic filamentous fungi, such as *Botrytis cinerea, Colletotrichum destructivum, Colletotrichum orbiculare, Fusarium oxysporum*, and *Pyricularia oryzae*.

In particular, a partial peptide of the peptide TsORF18-2 (SEQ ID NO: 40) preferably consists of, at least, 5 amino acid residues close to the C-terminus of the amino acid sequence as set forth in SEQ ID NO: 40, and more preferably consists of, at least, 8 amino acid residues close to the C-terminus thereof. It became clear that such partial peptides, that are more specifically, (a) amino acid sequence: ERTRKFWR (SEQ ID NO: 2), (b) amino acid sequence: RTRKFWRI (SEQ ID NO: 3), (c) amino acid sequence: TRKFWRIW (SEQ ID NO: 4), (d) amino acid sequence: RKFWRIWK (SEQ ID NO: 5), (e) amino acid sequence: KFWRIWKG (SEQ ID NO: 6), (f) amino acid sequence: FWRIWKGK (SEQ ID NO: 7), (g) amino acid sequence: WRIWKGKT (SEQ ID NO: 8), (h) amino acid sequence: RKFWR (SEQ ID NO: 9), (i) amino acid sequence: KFWRI (SEQ ID NO: 10), and (j) amino acid sequence: WRIWK (SEQ ID NO: 11) have extremely excellent germination inhibitory activity against plant pathogenic filamentous fungi.

Besides, partial peptides, which do not exhibit the germination inhibitory effects on the aforementioned plant pathogenic filamentous fungi in Table 3, are likely to exhibit the germination inhibitory effects, if various conditions such as a concentration are studied.

The invention claimed is:

1. A peptide, consisting of one amino acid sequence selected from the group consisting of the following (a) to (k):

(a) amino acid sequence: ERTRKFWR, (SEQ ID NO: 2)

(b) amino acid sequence: RTRKFWRI, (SEQ ID NO: 3)

(c) amino acid sequence: TRKFWRIW, (SEQ ID NO: 4)

(d) amino acid sequence: RKFWRIWK, (SEQ ID NO: 5)

(e) amino acid sequence: KFWRIWKG, (SEQ ID NO: 6)

(f) amino acid sequence: FWRIWKGK, (SEQ ID NO: 7)

(g) amino acid sequence: WRIWKGKT, (SEQ ID NO: 8)

(h) amino acid sequence: RKFWR, (SEQ ID NO: 9)

(i) amino acid sequence: KFWRI, (SEQ ID NO: 10) and (j) amino acid sequence: WRIWK. (SEQ ID NO: 11)

whereby said peptide exhibits antimicrobial activity.

2. A nucleic acid encoding the peptide according to claim 1.

3. A recombinant vector having the nucleic acid according to claim 2.

4. A transformant having the recombinant vector according to claim 3.

5. The transformant according to claim 4, wherein it is a plant cell or a plant body transformed with the recombinant vector.

6. A composition exhibiting sterilizing action or antimicrobial action against plant pathogens comprising the peptide according to claim 1.

7. An agricultural chemical comprising the peptide according to claim 1.

8. The agricultural chemical according to claim 7, which is for sterilizing or antimicrobial use against plant pathogens.

9. The agricultural chemical according to claim 8, wherein the plant pathogens are one or more plant pathogenic filamentous fungi selected from the group consisting of *Botrytis cinerea, Colletotrichum destructivum, Colletotrichum orbiculare, Fusarium oxysporum,* and *Pyricularia oryzae*.

10. The agricultural chemical according to claim 8, wherein the plant pathogen is *Xanthomonas oryzae* pv. *oryzae* or *Pseudomonas syringae* pv. *tomato*.

* * * * *